United States Patent [19]

Porteous

[11] Patent Number: 4,717,057

[45] Date of Patent: Jan. 5, 1988

[54] DENTAL PASTE CUP WITH INTEGRATED FINGER MOUNT

[76] Inventor: Don D. Porteous, 2794 Moraga Dr., Los Angeles, Calif. 90024

[21] Appl. No.: 4,543

[22] Filed: Jan. 16, 1987

[51] Int. Cl.⁴ .................. B65D 25/10; B65D 41/16
[52] U.S. Cl. ................... 224/217; 206/63.5; 215/100 A; 433/49; 433/97; 433/163
[58] Field of Search .......... D24/16; D27/14; 63/1 R, 63/1 SR, 15; 206/63.5, 368; 215/100 A; 224/217; 433/49, 97, 163

[56] References Cited

U.S. PATENT DOCUMENTS

| | | | |
|---|---|---|---|
| 292,963 | 2/1884 | Thie | 63/1 R |
| 1,856,619 | 5/1932 | Carsey | 224/217 |
| 2,222,741 | 11/1940 | Bush | 433/163 X |
| 2,539,940 | 1/1951 | Abramsom | 224/217 |
| 2,665,479 | 1/1954 | Weldon | 433/163 |
| 2,970,379 | 2/1961 | Hardgrove | 433/163 |
| 3,327,391 | 6/1967 | Malm | 206/63.5 |

Primary Examiner—Jimmy G. Foster
Attorney, Agent, or Firm—Donald Diamond

[57] ABSTRACT

A dental paste cup is provided which comprises a cup having an open mouth defined by a rim, a removable closure overlying the open mouth and engaging the rim, and a finger mount extending adjacently and circumferentially from the rim, in a ring-like manner, and terminating in an open end proximate to the rim to thereby provide a slide-resistant grip on a support finger. In a preferred embodiment, the closure is releasably secured to the inner rim of the cup and the open end segment of the finger mount, which is releasably attached to the outer rim of the cup, passes through an aperture in the finger mount into alignment with an outer extension of the closure. The application of a vertical squeezing force to the finger mount disengages the end segment from the rim and permits the end segment to bear against the outer extension of the closure and thereby effect displacement of the closure form the mouth of the cup.

10 Claims, 7 Drawing Figures

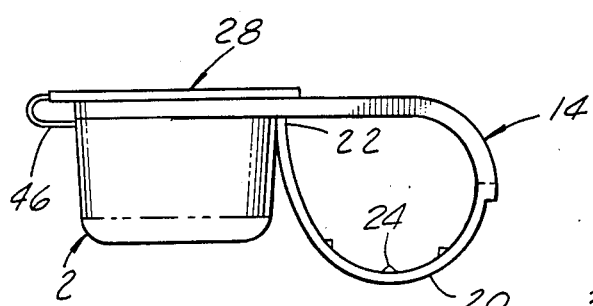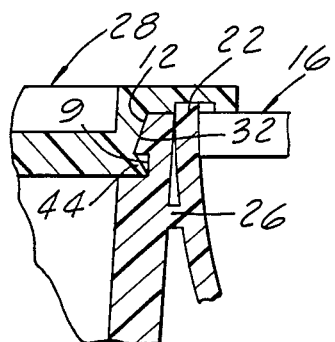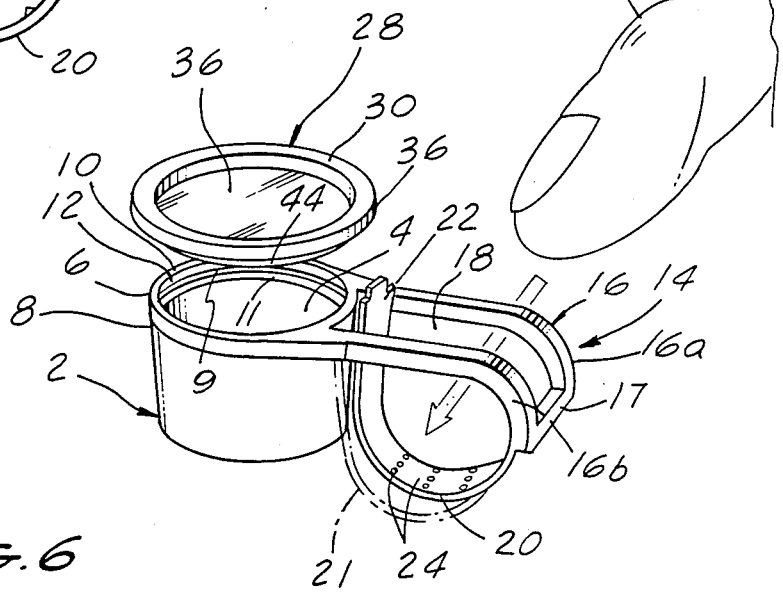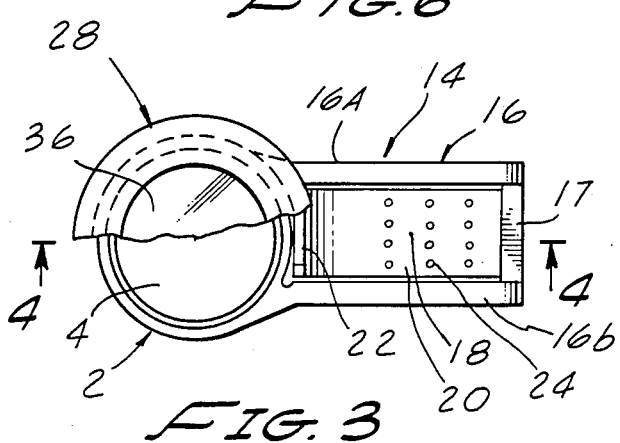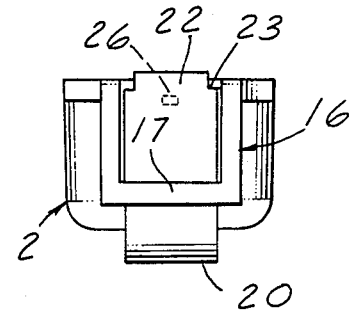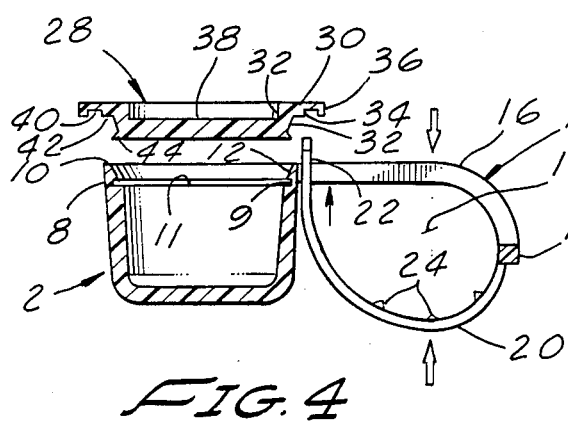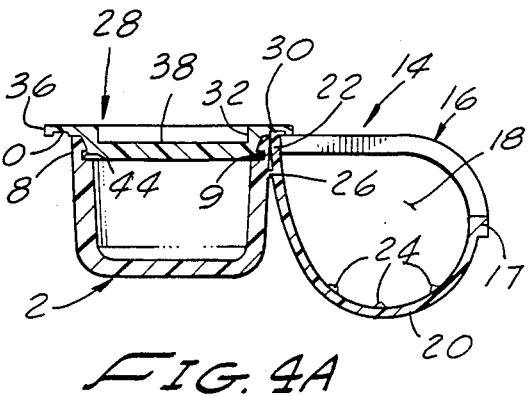

DENTAL PASTE CUP WITH INTEGRATED FINGER MOUNT

BACKGROUND OF THE INVENTION

1. Field of the Invention

This invention relates to dental paste cups and, more particularly, to dental paste cups which incorporate a finger mount having improved finger gripping characteristics.

2. Prior Art

In one packaging format, dental polishing paste adapted for use in dental practice has been supplied to the dental profession in disposable cups, sized for individual patient usage. In this format, the dental paste cup generally comprises a cylindrical container having an open mouth which is continuous with an outwardly disposed lateral flange. A closure in the form of a thin cover sheet overlies the mouth of the container and is secured to the upper surface of the lateral flange. The closure includes a laterally extending, pull-open tab to facilitate complete removal of the closure at the time of use and thereby permit unimpeded access to the dental paste in the container.

The aforesaid dental paste cup is adapted to be used with a sterilizable and reusable, metallic, finger-mountable, cup holder. In an illustrative prior art embodiment, the holder, which is constructed from thin sheet metal, generally comprises a cylindrical member that is continuous with an upwardly, outwardly and downwardly extending, finger-mountable member having its terminus in substantial spaced relationship to the cylindrical member. The finger-mountable member, in this embodiment, has an inverted U-shaped or horseshoe-like configuration. In use, the body of the dental paste cup is passed through the cylindrical member so as to engage the top of this member with the underside of the cup's lateral flange. The U-shaped finger mount is then passed over the finger which provides a support for the holder-cup combination. Thereafter, the clinician removes the closure from the dental paste cup and dips the tip of a power actuated applicator into the cup to thereby obtain a suitable quantity of dental paste for use in polishing a patient's teeth. A significant problem associated with the repeated use of dental cup holders incorporating U-shaped finger grips is that such holders tend to slip and slide about the finger upon application of a dipping force to the contents of the dental cup.

SUMMARY OF THE INVENTION

Accordingly, an important object of this invention is to provide an integrated dental paste cup and finger mount which has improved finger-gripping characteristics to thereby resist slipping and sliding about the finger when force is applied to the cup in connection with the removal of dental paste.

Another object of this invention is to provide an integrated dental paste cup and finger mount together with a cover for the cup which are formed by the conversion of a suitable molding resin into finished packaged components that are adapted to be assembled into a finished product containing dental paste, for individual usage, wherein the package is discarded after use to thereby save the time, cost and inconvenience involved in the sterilization of the metallic cup holders of the prior art.

These and other objects, features and advantages are accomplished by providing a dental paste cup comprising a cup having an open mouth defined by a rim, a removable closure overlying the open mouth and engaging the rim, and a finger mount extending circumferentially in an outward and downward direction from the rim of the cup and terminating in an open end proximate to the rim to thereby provide a slide-resistant grip on a support finger.

The rim of the cup includes an inner surface, a top surface and an outer surface with the inner surface advantageously being recessed and provided with a circumferential groove at its lower end. The removable closure has a substantially rigid construction and includes a laterally disposed peripheral flange that overlies the top of the rim and extends outwardly therefrom to thereby define an outer extension. The removable closure further includes a depending portion that is seated about and in slidable engagement with the inner surface of the rim. The lower end of the depending portion is advantageously provided with an outwardly disposed lateral tongue that is releasably engaged by the rim groove for releasably securing the closure to the cup.

The finger mount includes an aperture therethrough that extends outwardly from the cup rim. The open end of the finger mount passes through the aperture and into alignment with the underside of the closure outer extension whereby the application of a vertical squeezing force to the finger mount disengages the closure from the cup. To facilitate alignment of the open end of the finger mount with the outer extension of the closure, the finger mount can be releasably secured to the cup through a manually frangible connector disposed at or near the outer surface of the rim.

In contrast to the separate dental paste cup and metallic holder of the prior art, the present invention provides a disposable dental paste cup with an integrated finger mount having enhanced finger gripping characteristics to thereby resist slipping and sliding during use and, additionally, the integrated finger mount can be utilized to remove the closure from the cup.

The dental paste cup of this invention is readily manufactured from conventional materials by generally known methods of manufacture. A particularly suitable method of manufacture is injection molding of polyethylene resin, or similar plastic material, to thereby obtain components which, in assembled form, define a dental paste enclosure having an integrated finger mount for enhanced clinical usage.

DESCRIPTION OF THE DRAWINGS

FIG. 1 is a side elevational view of an embodiment of the present invention showing a dental paste cup and closure therefor, with the closure having an outer extension and the cup incorporating an integrated finger mount having an open end segment disposed proximate to the rim of the cup;

FIG. 2 is a diagrammatic view of the dental paste cup depicted in FIG. 1 and shows the finger mount provided with an aperture through which the open end segment passes to engage and effect removal of the closure from the cup;

FIG. 3 is a top plan view of the dental paste cup depicted in FIG. 1 and shows the closure in fragmentary section to further show the open end of the finger mount disposed within a channel on the underside of the closure outer extension;

FIG. 4 is a transverse section along line 4—4 of FIG. 3;

FIG. 4a is a transverse section similar to FIG. 4 showing the closure engaging the cup rim and the finger mount attached to the cup by a frangible connector;

FIG. 5 is a rear elevational view of the dental paste cup depicted in FIG. 1, with the cover removed; and FIG. 6 is an enlarged, fragmentary, sectional view showing the tongue and groove assembly for releasably holding the closure to the cup.

DETAILED DESCRIPTION

Referring now to the drawings and, in particular, FIGS. 1 and 2, there is shown a dental paste cup comprising a cup body 2 and a closure therefor 28, with the cup body being provided with an integrated finger mount 14.

The cup body 2 has an open mouth 4 defind by a rim 6 having an outer surface 8, a top surface 10 and an inner surface 12, with the inner surface of the rim being recessed and forming a shoulder 11 with the inner wall of the cup body. The lower end of the rim inner surface is provided with a circumferential groove 9.

The finger mount 14 extends outwardly from the rim of the cup, in a ring-like manner, and terminates in an open end segment 22 proximate to the cup outer rim 8, with the end segment including peripheral shoulder portion 23. The finger mount includes a first portion 16 and a second portion 20, with the first portion being formed by a pair of members 16a and 16b that are separated by an aperture 18 and joined at their distal ends by a cross-bar 17. The end sections of the members forming the first portion, as shown in FIGS. 1, 2 and 4, curve downwardly to the cross-bar 17 and the second portion 20 of the finger mount extends downwardly from the cross-bar and is curved inwardly and upwardly to terminate in the end segment 22 which passes through the aperture 18 into a position proximate to the cup outer rim. As shown in FIG. 2, the curvatures of the first portion 16 and the second portion 20 of the finger mount define an opening through which a finger 19 may be inserted and which serve to releasably grip the finger to thereby retain the cup 2 in a desired position on the finger. A plurality of ridges or risers 24 may advantageously be provided on the inner surface of the finger mount second portion 20 to enhance the gripping characteristics of the finger mount. A readily frangible connector 26 may advantageously be used to releasably secure the outer surface of the finger mount second portion 20 to the outer surface of the cup 2 at a locus proximate to the bottom of the rim outer surface 8. The frangible connector maintains the end segment 22 of the finger mount second portion in a suitable position and alignment to aid in the removal of closure 28 from the body of the cup.

The closure 28 releasably encloses the mouth 4 of the cup 2 and is formed with a peripheral flange 30 having a depending portion 32 and inner and outer skirts 34, 36. The depending portion 32 connects the peripheral flange 30 to the recessed closure surface 38 while the inner and outer skirts 34, 36 define an inverted channel 40. Inner skirt 34 forms a shoulder 42 with depending portion 32. The lower end of the depending portion 32 is provided with an outwardly disposed, circumferential tongue 44 that is adapted to be releasably engaged by the circumferential rim groove 9 to releasably secure the closure to the cup.

In the assembled package, the depending portion 32 of the closure 28 is seated about and in slidable engagement with the cup rim inner surface 12, the top of the cup rim 10 engages the closure shoulder portion 42, the closure tongue 44 is releasably engaged in the rim groove 9, the end segment 22 of the finger mount is releasably connected to the outer surface of the cup rim by a frangible connector 26, and the terminus of the end segment 22 is disposed within the closure inverted channel 40.

In use, the enclosed dental paste cup is provided to the clinician containing a dental paste or other suitable material for application to a patient. By applying a vertical squeezing force to the finger mount 14, as shown in FIG. 4, the clinician breaks the frangible connector 26 and causes the finger mount end segment 22 to disengage from a fixed position 21 and to bear against the outer extension of flange 30 which forces the closure tongue 44 out of the rim groove 9 and effects displacement of the closure from the mouth of the cup to thereby permit access to the contents within the cup. The clinician then inserts a finger 19 into the finger mount 14, where the curvature of the semi-rigid first portion 16, the curvature of the yieldable second portion 20, and the risers 24 on the inner surface of the second portion serve to prevent slipping and sliding of the finger mount on the support finger and to releasably retain the cup 2 in the desired position. The clinician then dips the tip of a power actuated applicator into the dental paste cup to obtain a suitable quantity of dental paste which is applied to a dental area in the usual manner. Upon completion of this aspect of the treatment, the dental paste cup, which is sized for individual patient usage, is discarded.

In a further embodiment of this invention, the closure 28 is pivotally hinged to the outer surface of the cup body 2 by a frangible strap hinge 46, as shown in FIG. 1. The attachment of the closure to the cup body through the strap hinge facilitates final assembly of the packaged product. Since the strap hinge has a frangible construction, it can be readily severed by the clinician following displacement of the closure from the cup or the strap hinge can be severed by the packager after the cup is filled with dental paste and the closure is secured to the rim of the cup.

The principal components of the dental paste cup, namely, the closure 28 and the cup 2 with an integrated finger mount 14 may be readily manufactured by utilizing customary molding techniques with a suitable plastic resin such as polyethylene, polypropylene and the like.

While in the foregoing description and accompanying drawings, there has been shown and described the preferred embodiment of this invention, it will be understood, of course, that minor changes may be made in the details of construction as well as in the combination and arrangement of parts without departing from the spirit and scope of the invention as claimed.

That which is claimed is:

1. A Dental Paste Cup comprising:
   a cup having an open mouth defined by a rim that includes an inner surface, a top surface and an outer surface;
   a removable closure overlying said open mouth and engaging said rim, said removable closure having a substantially rigid construction and including a laterally disposed peripheral flange that overlies the top surface of said rim and extends outwardly therefrom to thereby define an outer extension; and a finger mount extending circumferentially in an outward and downward direction from the rim of said cup and terminating in an open end proximate to said rim to thereby provide a slide-resistant grip on a support finger, said finger mount being defined by first and second portions, with said first portion projecting from the rim of the cup and having an aperture therethrough that extends outwardly from said rim, and said second portion terminates in said open end that passes through the aperture of said first portion and into alignment with the underside of the outer extension of the peripheral flange of said closure, whereby the application of a vertical squeezing force to said finger mount disengages said closure from said cup.

2. The dental paste cup of claim 1 wherein said closure includes a depending portion seated about and in slideable engagement with the inner surface of said rim.

3. The dental paste cup of claim 2 wherein the closure depending portion and the inner surface of said rim include cooperating means for releasably securing said closure to said cup.

4. The dental paste cup of claim 3 wherein the cooperating means comprise (i) a lateral tongue outwardly disposed at the lower end of said closure depending portion and (ii) a groove disposed in the lower end of the inner surface of said rim for releasably engaging said lateral tongue.

5. The dental paste cup of claim 4 wherein the inner surface of said rim is recessed.

6. The dental paste cup of claim 2 wherein the top surface of the closure, within the area defined by the depending portion, is recessed.

7. The dental paste cup of claim 1 wherein the first portion of the finger mount is semi-rigid and the second portion of the finger mount is yieldable.

8. The dental paste cup of claim 1 wherein a plurality of risers extend from the inner, finger engaging surface of the second portion of said finger mount.

9. The dental paste cup of claim 1 wherein the second portion of said finger mount is releasably attached to said cup through manually frangible connector means disposed at or proximate to the rim outer surface.

10. The dental paste cup of claim 1 wherein the underside of said peripheral flange outer extension is provided with an inverted channel and the open end of the finger mount second portion is disposed in said channel.

* * * * *